United States Patent
Gamache

(10) Patent No.: US 10,408,763 B2
(45) Date of Patent: Sep. 10, 2019

(54) SYSTEMS AND METHODS FOR TESTING FOR A GAS LEAK THROUGH A GAS FLOW COMPONENT

(71) Applicant: Mécanique Analytique Inc., Thetford-Mines (CA)

(72) Inventor: Yves Gamache, Thetford-Mines (CA)

(73) Assignee: Mécanique Analytique Inc., Thetford-Mines, QC (CA)

(*) Notice: Subject to any disclaimer, the term of this patent is extended or adjusted under 35 U.S.C. 154(b) by 106 days.

(21) Appl. No.: 15/545,974

(22) PCT Filed: Jan. 29, 2016

(86) PCT No.: PCT/CA2016/050072
§ 371 (c)(1),
(2) Date: Jul. 24, 2017

(87) PCT Pub. No.: WO2016/119060
PCT Pub. Date: Aug. 4, 2016

(65) Prior Publication Data
US 2018/0003641 A1 Jan. 4, 2018

Related U.S. Application Data

(60) Provisional application No. 62/109,915, filed on Jan. 30, 2015.

(51) Int. Cl.
*G01M 3/20* (2006.01)
*G01M 3/22* (2006.01)
(Continued)

(52) U.S. Cl.
CPC ............ *G01N 21/73* (2013.01); *G01M 3/20* (2013.01); *G01M 3/38* (2013.01)

(58) Field of Classification Search
CPC ............ G01M 3/20; G01M 3/22; G01M 3/38; G01N 21/62; G01N 21/73; G01N 25/20
See application file for complete search history.

(56) References Cited

U.S. PATENT DOCUMENTS

| 4,147,431 A | 4/1979 | Mann |
| 4,270,091 A | 5/1981 | Mann |

(Continued)

FOREIGN PATENT DOCUMENTS

| EP | 1568987 B1 | 1/2009 |
| EP | 1914532 B1 | 12/2012 |

(Continued)

OTHER PUBLICATIONS

International Search Report and the Written Opinion of the International Searching Authority corresponding to International Patent Application No. PCT/CA2016/050072 (10 pages) (dated Apr. 18, 2016).

(Continued)

*Primary Examiner* — Nguyen Q. Ha
(74) *Attorney, Agent, or Firm* — Myers Bigel, P.A.

(57) ABSTRACT

Methods and systems of testing for a gas leak between an inlet zone and an outlet zone of a gas flow component in a shut state are provided. Different tracer and carrier gases are used. The carrier gas is circulated through the outlet zone of the gas flow component to purge the tracer gas from this outlet zone. A spectroscopic emission from the carrier gas indicative of an amount of the purged tracer gas is monitored. A test flow of the tracer gas is introduced in the inlet zone of the gas flow component, and the inlet pressure is increased for successive pressure increments. The presence of a gas leak is determined upon detecting an intensity step variation in the monitored spectroscopic emission following one of the pressure increments in the inlet pressure.

29 Claims, 6 Drawing Sheets

(51) Int. Cl.
*G01M 3/38* (2006.01)
*G01N 21/62* (2006.01)
*G01N 21/73* (2006.01)

(56) References Cited

U.S. PATENT DOCUMENTS

| | | | |
|---|---|---|---|
| 4,715,213 A * | 12/1987 | McGreehan | G01M 3/20 277/320 |
| 5,326,975 A | 7/1994 | Barna | |
| 5,528,923 A | 6/1996 | Ledez et al. | |
| 5,681,983 A | 10/1997 | Seigot | |
| 5,789,754 A | 8/1998 | Cathey et al. | |
| 6,050,133 A * | 4/2000 | Achter | A61L 2/28 73/40.7 |
| 6,164,116 A | 12/2000 | Rice et al. | |
| 7,385,681 B2 | 6/2008 | Ninomiya et al. | |
| 7,403,283 B2 | 7/2008 | Sogan et al. | |
| 7,590,498 B1 | 9/2009 | Chung et al. | |
| 9,841,345 B2 * | 12/2017 | Bounouar | G01M 3/229 |
| 2006/0006139 A1 | 1/2006 | Johnson et al. | |
| 2007/0157704 A1 * | 7/2007 | Jenneus | G01M 3/226 73/40.7 |
| 2009/0229348 A1 | 9/2009 | Woo | |
| 2009/0277249 A1 * | 11/2009 | Polster | G01M 3/229 73/40.7 |
| 2010/0018293 A1 | 1/2010 | Monkowski et al. | |
| 2011/0247400 A1 | 10/2011 | Schwartz et al. | |
| 2011/0290006 A1 | 12/2011 | Perkins et al. | |
| 2012/0228872 A1 | 9/2012 | Gamache | |
| 2015/0068288 A1 * | 3/2015 | Gaudet | F17D 5/04 73/40.7 |
| 2015/0362467 A1 * | 12/2015 | Wetzig | G01M 3/002 73/25.03 |

FOREIGN PATENT DOCUMENTS

| | | |
|---|---|---|
| JP | 2000028471 A | 1/2000 |
| RU | 2494362 C1 | 9/2013 |
| WO | 2004079350 A1 | 9/2004 |
| WO | 2006089412 A1 | 8/2006 |
| WO | 2011012730 | 2/2011 |
| WO | 2014016308 A1 | 1/2014 |

OTHER PUBLICATIONS

Ho Jae Lee et al., Use of In-Situ Optical Emission Spectroscopy for Leak Fault Detection and Classification in Plasma Etching, Journal of Semiconductor Technology and Science, vol. 13, No. 4, Aug. 2013, pp. 395-401.

Kontrol Analytik (Contrôle Analytique Inc.), K2001ns TRACE N2 Analyzer User's Manual, Version 4.5, Jul. 1999, p. 86.

* cited by examiner

SYSTEMS AND METHODS FOR TESTING FOR A GAS LEAK THROUGH A GAS FLOW COMPONENT

TECHNICAL FIELD

The present invention generally relates to detection of a gas leak from a component, and more particularly to a system and related method for gas leak detection based on spectroscopic emission of the gas.

BACKGROUND

The integrity of components such as valves, fittings or vessels used for gas chromatography or other analytical systems is an important factor in the precision as well as the security of such systems. These components therefore need to be tested prior to installation and periodically once in use to detect the presence of any leaks through the component so that appropriate action can be taken.

Manners of detecting a gas leak in a component include detection with a carrier gas and a tracer gas. For example, it is known in the art to use helium as a tracer gas. The component to be tested is vacuum pumped and connected on one side to a mass spectrometer tuned to detect helium only. The component is normally exposed to atmospheric air, where generally speaking, there is a 5 ppm helium content. In other variants, a helium cylinder may be used so that a higher concentration of helium is allowed to leak through inside the component, and be detected by the mass spectrometer.

Helium-based leak detection systems can however be expensive, as a complete mass spectrometer carries a high cost, in addition to a vacuum pump, vacuum hardware, etc. Furthermore, helium suffers from a supply shortage and several attempts to replace helium in analytical systems have been documented.

The sensitivity and performance of known leak detection systems can also depend on the type of leak present in the component under test. Gas leaks may be classified under three types: orifice-type leaks, capillary-type leaks and permeation-type leaks.

A gas leak can generally be defined as the circulation of a gas from one area (for example, an inlet zone) to another area (for example, an outlet zone) and through a flow channel.

An orifice-type leak corresponds to a leak wherein the length of the flow channel is at most identical to its average diameter. Typically, orifice-type leaks can appear through the wall of a vessel or gas canister, tubing or fitting with inadequate sealing area, etc. Gases of low molecular size, like hydrogen, flowing easily through the orifice channel may be unsafe to use for detecting this type of gas leak.

A capillary-type leak corresponds to a leak wherein the length of the flow channel is much longer than its average diameter. Capillary-type leaks can appear in various valve configurations including globe, ball, butterfly, gate, etc. Capillary-type leaks can also appear through fittings, generally because they are not properly tightened or because the surface of the fitting wall is porous or scratched. Gases of low viscosity flow more easily through capillary channels.

A permeation-type leak corresponds to a leak wherein the flow channel is created by diffusion of gas molecules through an interface. Usually, gas molecules will move from a high concentration zone to a low concentration zone across the interface. For example, permeation-type leaks can appear in valves under high pressure through plastic or polymer sealing device, like gaskets and O-rings. It can also appear through thin metal walls and membranes. Gas permeation may be influenced by temperature and high pressures.

Leak detection systems and method should take under consideration the type or types of leaks to be detected. It would also be advantageous to provide such systems and method which enable the detection or different types of leaks.

There is thus a need for a technology that overcomes at least some of the drawbacks of what is known in the field.

SUMMARY

The present invention responds to the above need by providing a system and a related method for testing for, and detecting, a gas leak in a gas flow component upon identification of a variation pattern in the spectroscopic emission of the gas.

In accordance with one aspect there is provided a method of testing for a gas leak between an inlet zone and an outlet zone of a gas flow component in a shut state, the method using a tracer gas and a carrier gas different from the tracer gas. The method includes:
  circulating the carrier gas through the outlet zone of the gas flow component to purge the tracer gas from said outlet zone;
  monitoring, using a plasma emission detector downstream of the outlet zone, a spectroscopic emission from the carrier gas indicative of an amount of the tracer gas purged from the outlet zone;
  upon said monitoring indicating that a residual amount of said tracer gas has been purged from the outlet zone, introducing a test flow of the tracer gas in the inlet zone of the gas flow component;
  increasing an inlet pressure of the gas flow component for at least one pressure increment; and
  determining a presence of a gas leak between the inlet zone and outlet zone of the gas flow component upon detecting a step variation in the monitored spectroscopic emission following one of said pressure increments in the inlet pressure.

In some implementations the method may include a preliminary step of pre-purging the outlet zone of atmospheric air.

In one implementation the carrier gas consists of argon and the tracer gas consists of nitrogen. In another implementation the carrier gas consist of helium and the tracer gas consists of argon.

The step of monitoring the spectroscopic emission may include displaying, as a function of time, an intensity of a spectroscopic emission signal representative of said monitored spectroscopic emission on a normalized intensity scale. A step of re-scaling the spectroscopic emission signal upon said monitoring indicating that the residual amount of said tracer gas has been purged from the outlet zone may be provided.

The step of monitoring the spectroscopic emission may involve parallelly monitoring the spectroscopic emission at a first wavelength and at a second wavelength respectively sensitive to a first range and a second range of the tracer gas concentration in the outlet zone of the component.

The method may also include recycling the carrier gas to the outlet zone after monitoring the spectroscopic emission.

In accordance with another aspect, there is also provided a leak testing system for testing for a gas leak between an inlet zone and an outlet zone of a gas flow component in a shut state using a tracer gas and a carrier gas different from the tracer gas.

The system includes a pressurizing unit connectable to the gas flow component so as to be in fluid communication with the inlet zone. The pressurizing unit is configured to be fed with the tracer gas and to deliver a test flow of this tracer gas into the inlet zone of the gas flow component. The pressurizing unit is operable to increase an inlet pressure of the gas flow component for successive pressure increments;

The system also includes a carrier gas flow control assembly connectable to the gas flow component so as to be in bidirectional fluid communication with the outlet zone of the gas flow component. The carrier gas flow control assembly is configured to receive an input carrier gas flow and circulate the same through the outlet zone of the gas flow component to purge the tracer gas from said outlet zone, resulting in an output carrier gas flow The system further includes a monitoring device connectable to the carrier gas flow control assembly so as to receive the output carrier gas flow, the monitoring device including a plasma emission detector and being configured to monitor a spectroscopic emission from the output carrier gas flow indicative of an amount of the tracer gas purged from the outlet zone.

The system finally includes a processing device in communication with the monitoring device to receive the monitored spectroscopic emission therefrom. The processing device is configured to allow a determination of a presence of a gas leak between the inlet zone and outlet zone of the gas flow component upon detecting an intensity variation pattern in the monitored spectroscopic emission following one of said pressure increments in the inlet pressure.

In some implementations the system may further include a sieving assembly operable to sieve the output carrier gas flow upstream of the monitoring device, the sieving assembly comprising at least one of a moisture trap and a hydrocarbon trap. A moisture doping device operable to provide a doping amount of water to the output carrier gas flow upstream of the monitoring device may also be included.

In some implementations the pressurizing unit includes a pressure transducer for measuring the inlet pressure and a high pressure electronic pressure controller for varying the inlet pressure.

In some implementations the carrier gas flow control assembly is switchable between:
  an open position for venting the output carrier gas flow to the atmosphere, and
  a closed position for guiding the output carrier gas flow to the monitoring device.

The processing device may include a first signal processing channel and a second signal processing channel, respectively configured to monitor the spectroscopic emission at a first wavelength and at a second wavelength respectively sensitive to a first range and a second range of the tracer gas concentration in the outlet zone of the component.

In some implementations the system may further include a gas recycling assembly downstream of the monitoring device, to recycle at least a part of the carrier gas from the monitoring device to the outlet zone of the gas flow component.

The monitoring device may include a photodiode transforming light emitted by a plasma within the Plasma Emission Detector into a proportional analog or digital signal.

In accordance with yet another aspect there is also provided a method of testing for a gas leak between an inlet zone and an outlet zone of a gas flow component in a shut state. The method uses a tracer gas and a carrier gas different from the tracer gas, the method includes:
  exposing the inlet zone of the gas flow component to the tracer gas;
  circulating the carrier gas through the outlet zone of the gas flow component to purge the tracer gas from said outlet zone according to a constant volume flow rate;
  monitoring, using a plasma emission detector downstream of the outlet zone, a spectroscopic emission from the carrier gas indicative of an amount of the tracer gas purged from the outlet zone;
  upon said monitoring indicating that a residual amount of said tracer gas has been purged from the outlet zone, decreasing the volume flow rate of the carrier gas for at least one flow rate decrement; and
  determining a presence of a gas leak between the inlet zone and outlet zone of the gas flow component upon detecting a step in the monitored spectroscopic emission following one of said volume flow rate decrement.

In accordance with embodiments of this method a preliminary step of pre-purging the outlet zone of atmospheric air may be provided. The tracer gas may consist of nitrogen and the step of exposing the inlet zone of the gas flow component to the tracer gas comprises exposing said inlet zone to ambient air. The carrier gas may consist of argon. The step of monitoring the spectroscopic emission may include displaying, as a function of time, an intensity of a spectroscopic emission signal representative of said monitored spectroscopic emission on a normalized intensity scale. The method may include a step of re-scaling the spectroscopic emission signal prior to said at least one flow rate decrement. The step of monitoring the spectroscopic emission may include parallelly monitoring the spectroscopic emission at a first wavelength and at a second wavelength respectively sensitive to a first range and a second range of the tracer gas concentration in the outlet zone of the component. The method may also involve recycling the carrier gas to the outlet zone after monitoring the spectroscopic emission.

In accordance with yet another aspect there is also provided a method of testing for a gas leak between an inlet zone and an outlet zone of a gas flow component in a shut state, the method using a tracer gas and a carrier gas different from the tracer gas. The method includes:
  circulating the carrier gas through the outlet zone of the gas flow component to purge the tracer gas from said outlet zone;
  exposing the inlet zone of the gas flow component to the tracer gas;
  parallelly monitoring, using a plasma emission detector downstream of the outlet zone, a spectroscopic emission from the carrier gas indicative of an amount of the tracer gas purged from the outlet zone at a first wavelength and at a second wavelength respectively sensitive to a first range and a second range of the tracer gas concentration in the outlet zone of the component.

In some implementations the carrier gas may consist of argon and the tracer gas may consist of nitrogen. When the tracer gas is nitrogen, the first and second wavelengths can for example be selected from nitrogen spectroscopic lines at 337.1 nm, 391.0 nm. In other implementations the carrier gas may consist of helium and the tracer gas may consist of argon.

In some implementations the step of monitoring the spectroscopic emission may include displaying, as a function of time, an intensity of a spectroscopic emission signal representative of said monitored spectroscopic emission at each of the first and second wavelengths on a corresponding normalized intensity scale.

In one aspect, there is provided a method for detecting a gas leak between an inlet zone and an outlet zone of a component. The method includes:

circulating a carrier gas through the outlet zone of the component to gradually purge a residual amount of a tracer gas from said outlet zone;

monitoring, downstream of the outlet zone of the component, a spectroscopic emission from the carrier gas indicative of the gradual purge of the tracer gas from the outlet zone;

introducing a test flow of the tracer gas in the inlet zone of the component at an incrementally increasing inlet pressure; and determining a presence of the gas leak between the inlet zone and outlet zone of the component upon detecting an intensity variation pattern in the monitored spectroscopic emission following an incremental increase in the inlet pressure.

In some implementations, the intensity variation pattern may include an intensity variation step following the incremental increase in the inlet pressure. Further optionally, the intensity variation pattern may include a decreasing intensity variation over time following the incremental increase in the inlet pressure.

In some implementations, the carrier gas may include argon or helium. The tracer gas may include nitrogen or argon.

In some implementations, the step of monitoring the spectroscopic emission may include selectively monitoring the spectroscopic emission at a first wavelength and at a second wavelength respectively sensitive to a first range and a second range of the tracer gas concentration in the outlet zone of the component. Optionally, the tracer gas may be nitrogen and the first wavelength may be 337.1 nm and the second wavelength may be 391 nm.

In some implementations, each incremental increase in the inlet pressure may be performed after a pre-set operating time during the introduction of the test flow of the tracer gas. Optionally, the pre-set operating time may be chosen to monitor an asymptotic intensity variation in the spectroscopic emission by the end of said pre-set operating time. Further optionally, the pre-set operating time may be further chosen so that the intensity variation tends to be null by the end of said pre-set operating time.

In some implementations, the method may include pre-purging the outlet zone from atmospheric air before monitoring. The pre-purging may include circulating the carrier gas until that the outlet zone contains the residual amount of tracer gas.

In some implementations, the method may include recycling the carrier gas to the outlet zone after monitoring the spectroscopic emission.

In some implementations, the method may include molecularly sieving the carrier gas to eliminate at least a quantity of the tracer gas before recycling to the outlet zone.

In some implementations, the method may include introducing a first test flow of tracer gas in the inlet zone of the component at the incrementally increasing inlet pressure for detection of gas leaks of a first range of concentration in the carrier gas; and introducing a second test flow of another tracer gas in the inlet zone at the incrementally increasing inlet pressure for detection of gas leaks of a second range of concentration in the carrier gas.

In another aspect, there is provided a system for detecting a gas leak between an inlet zone and an outlet zone of a component. The system includes:

a pressurizing unit connectable to the component so as to be in fluid communication with the inlet zone, the pressurizing unit being configured to be fed with a tracer gas and to deliver a test flow of the tracer gas into the inlet zone of the component at an incrementally increasing pressure;

a monitoring device connectable to the component so as to be in fluid communication with the outlet zone, the monitoring device being configured to monitor spectroscopic emission from a carrier gas flowing therethrough to gradually purge a residual amount of the tracer gas from said outlet zone, the monitored spectroscopic emission being indicative of the gradual purge of the tracer gas from said outlet zone; and a processing device in connection to the monitoring device to receive the monitored spectroscopic emission, the processing device being configured to detect a presence of the gas leak between the inlet zone and outlet zone of the component upon displaying an intensity variation pattern in the monitored spectroscopic emission following an increment in the inlet pressure.

In some implementations, the system may include a sieving assembly connectable to the outlet zone of the component to sieve the carrier gas from the outlet zone upstream of the monitoring device, the sieving assembly comprising at least one of a moisture trap and a hydrocarbon trap. Optionally, the moisture trap may include a 3 Å molecular sieve. Further optionally, the hydrocarbon trap may include an activated charcoal, a nickel-based catalyst or any other hydrocarbon active gettering material.

In some implementations, the system may include a moisture doping device connectable to the outlet zone of the component to provide a doping amount of water to the carrier gas upstream of the monitoring device. Optionally, the doping amount of water may range between 3 ppm and 8 ppm.

In some implementations, the pressurizing unit may include a pressure transducer for measuring the inlet pressure and a high pressure electronic pressure controller for varying the inlet pressure.

In some implementations, the system may include a valve assembly in fluid communication with either the inlet zone or the outlet zone of the component, the valve assembly being switchable between an open position for venting the tracer gas or the carrier gas to the atmosphere, and a closed position for guiding the carrier gas and tracer gas to the monitoring device.

In some implementations, the processing device may include a first signal processing channel and a second signal processing channel, the first signal processing channel being used to display the monitored spectroscopic emission and the second signal processing channel being used to display a differential spectroscopic emission according to the residual amount of tracer gas.

In some implementations, a gas recycling assembly connectable to the outlet zone of the component and downstream of the monitoring device, to recycle at least a part of the carrier gas from the monitoring device to the outlet zone of the component. Optionally, the gas recycling assembly may include at least one of a pump, a purifier for removing at least a part of the tracer gas from the carrier gas and a flow restrictor to provide an adequate flow rate of carrier gas into the outlet zone. Further optionally, the flow restrictor may be a capillary flow orifice. Further optionally, the monitoring device may be an atomic or molecular emission spectroscope comprising a plasma emission detector.

In some implementations, the system may be configured to be portable.

While the present invention will be described in conjunction with example embodiments, it will be understood that it is not intended to limit the scope of the invention to such embodiments. On the contrary, it is intended to cover all alternatives, modifications and equivalents as may be included as defined in the present description and appended claims. The objects, advantages and other features of the present invention will become more apparent and be better understood upon reading of the following non-restrictive description of the invention, given with reference to the accompanying drawings.

BRIEF DESCRIPTION OF THE DRAWINGS

Implementations of the gas leak testing system and method are represented in and will be further understood in connection with the following figures.

DETAILED DESCRIPTION OF EMBODIMENTS

Figure 1:
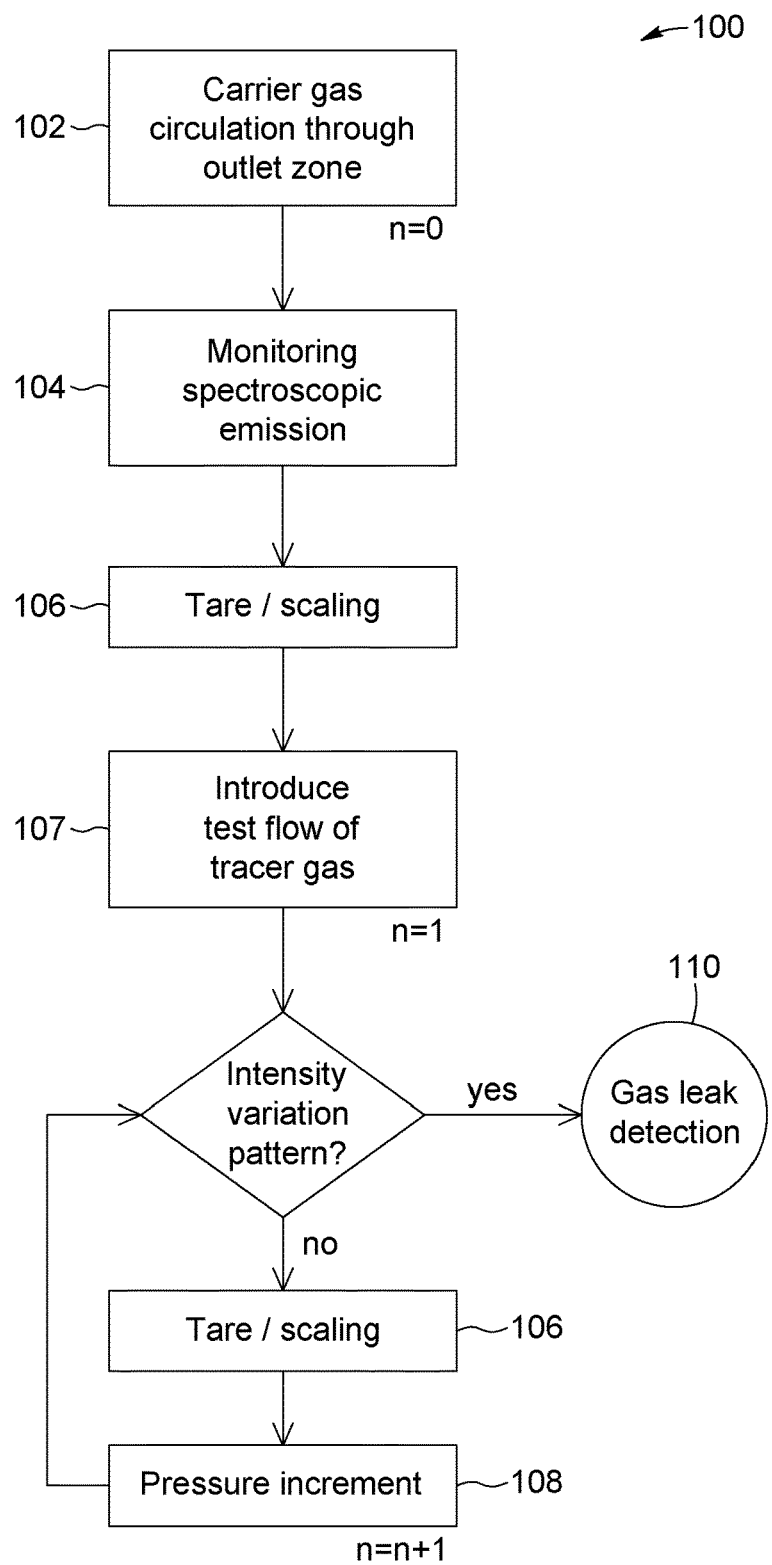
FIG. 1 is a schematic diagram of the gas leak testing method steps according to an embodiment of the present invention.

In accordance with aspects of the invention, there are provided methods and systems making use of spectroscopic emission techniques to detect various types of gas leaks from a gas flow component.

It will be readily understood that the gas flow component may be embodied by various devices through which analytical gases can circulate. In some implementations the gas flow component may be a valve, such as for example a diaphragm valve, rotary valve, needle valve, ball valve, etc. In other implementations the gas flow component may be a fitting, a vessel or the like. In additional implementations, the gas flow component may be a system or assembly composed of several elements, such as for example a sampling line. The gas flow component is assumed to allow a gas flow therethrough, and therefore includes an inlet zone through which gas is inserted and an outlet zone from which gas exits the gas flow component. It will be readily understood that the identification of the inlet and outlet zone may depend on the type of gas flow component and on the context in which it is being used. Indeed, if the gas flow component is symmetrical with respect to its input and output ends, either ends of the gas flow component may be designated as the inlet or outlet zone for the purpose of the present gas leak testing method.

The gas-flow component may be part of, or destined for use in, a gas-based analytical system, for example in applications such as chromatography, gas analysers, sampling lines, etc. In some implementations, the gas flow component may be tested within its operating environment, by connecting the inlet and outlet zones to a leak testing system such as described herein or other assembly capable of performing the described testing method. In other implementations, the gas flow component may be removed from its operating environment and tested according to the present method in a different location. In yet another implementation, the gas flow component may be a new component tested according to the method described herein prior to being used.

The leak testing method and systems described herein use a tracer gas and a carrier gas different from the tracer gas.

The tracer gas may be embodied by any gas species apt to flow from the inlet zone to the outlet zone of the gas flow component in the presence of a leak path through this component. In one embodiment, the tracer gas may for example be nitrogen ($N_2$). The use of nitrogen may present several benefits. Firstly, nitrogen molecules are small enough and have a viscosity sufficiently low to allow circulation through capillary-type leak paths. Furthermore, sources of nitrogen can be obtained at a relatively low price. In some implementations, ambient air can simply be used as the source of tracer gas, since the nitrogen content in air is of 79%. Although passages of the description below refer to nitrogen as the tracer gas, in other implementations, however, other species of tracer gases can be used, such as for example helium or argon.

The carrier gas may be embodied by a gas suitable for use as a means of fluid communication through the outlet zone, and for carrying the tracer gas away from the outlet zone. The carrier gas may for example be embodied by argon, helium or a combination thereof. It should be understood that the carrier gas is not limited to argon or helium and can include any suitable gases based on the characteristics of the gas flow component under test and the magnitude of the gas leak.

As will be readily understood by one skilled in the art, prior to being tested according to the present method, the gas flow component under test is in a shut state, that is, shut tight such that circulation of tracer gas between the inlet zone and the outlet zone should normally be prevented. Gas leaks detected through the present method are therefore indicative of the presence of an undesired flow path through the gas flow component in its shut state.

Testing Method Using Inlet Pressure Control

FIG. 1 shows a flow chart of a method 100 of testing for a gas leak between the inlet zone and the outlet zone of a gas flow component under test according to some embodiments.

It should be noted that the method according to embodiments may be used to test for leaks of various types, such as orifice-type, capillary-type and permeation-type leaks. As explained above, "orifice-type leaks" are typically high value leaks, as a substantive amount of tracer gas of low molecular weight, such as nitrogen, can leak through the corresponding orifice in the gas flow component. Capillary-type leaks and permeation-type leaks may be referred to as low value leaks, as the amount of tracer gas, even of low molecular weight such as nitrogen, that can leak through the gas flow component is substantially lower than for orifice-type leaks. Typically, gas concentration in the outlet zone in relation to high value leaks are of the order of 10,000 ppm, in comparison to sub-ppm or ppb for low value leaks. These values are given by way of example only and should not be considered limitative to the present invention.

Advantageously, embodiments of the present invention may be used to test for any of the different types of leaks mentioned above. For example, nitrogen can be used as tracer gas in combination with argon as carrier gas to detect sub-ppm to at least 10,000 ppm gas leaks. Wavelengths of interest for spectroscopic monitoring of nitrogen in argon for example include lines at 337.1 nm and/or 391.0 nm. Alternatively, for detection of gas leaks of ppb or ppt magnitude, argon can be used as tracer gas in combination with helium as carrier gas. Indeed, when using a plasma emission detector as a monitoring device, under the created helium plasma at atmospheric or sub-atmospheric pressure, ppb or ppt of argon in helium can be detected. A spectroscopic emission of argon in helium around 911 nm can for example be used. In some implementations, the method may include selecting a tracer gas or a carrier gas in view of the carrier gas or tracer gas respectively, considering the magnitude of the gas leak to be detected. For example, one skilled in the art can readily use within a same leak testing system any one of a plurality of tracer gas that are interchangeable so as to meet different sensitivity requirements and detect gas leaks from low value to high value from a same gas flow component under test.

Figure 2:
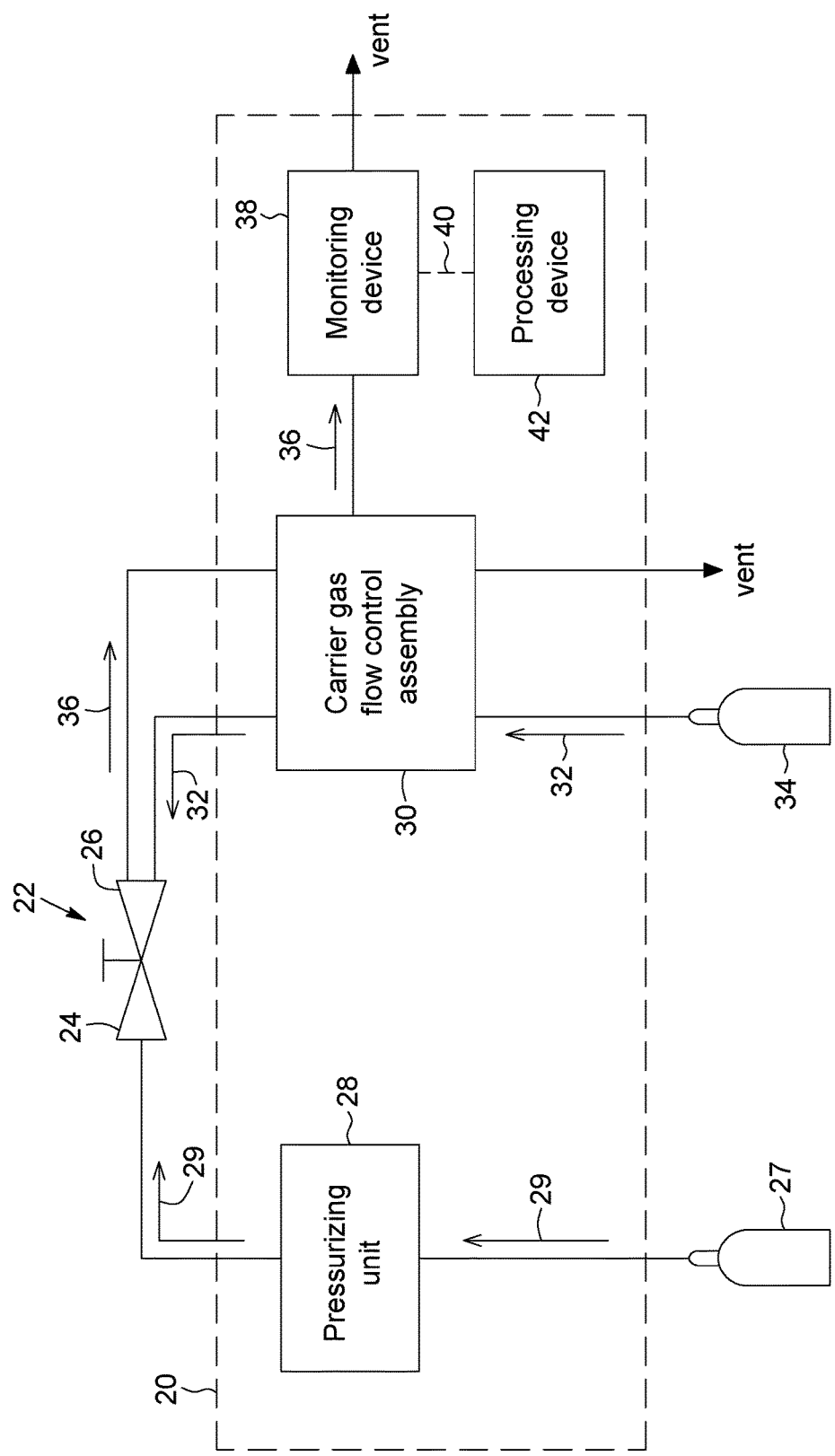
FIG. 2 is a schematic diagram of the gas leak testing system according to an embodiment of the present invention.

In some implementations, the method 100 described herein may be performed using a leak testing system 20 such as schematically illustrated in FIG. 2. The leak testing system 20 is shown connected to a gas flow component 22 (illustrated as a valve by way of example) having an inlet zone 24 and an outlet zone 26. The leak testing system 20 generally includes a pressurizing unit 28 in fluid communication with the inlet zone 24. The pressurizing unit 28 is configured to be fed with the tracer gas, optionally from a tracer gas source 27, and to deliver a tracer gas test flow 29 into the inlet zone 24 of the gas flow component 22. The leak testing system 20 further includes a carrier gas flow control assembly 30 in bidirectional fluid communication with the outlet zone 26. The carrier gas flow control assembly 30 is configured to receive an input carrier gas flow 32 from a carrier gas source 34. The input carrier gas flow 32 circulates through the outlet zone 26 of the gas flow component 22, purging tracer gas therefrom, as explained in more detailed below, resulting in an output carrier gas flow 36. The leak testing system 20 further includes a monitoring device 38 receiving the output carrier gas flow 36. The monitoring device 38 is configured to continuously monitor a spectroscopic emission from the output carrier gas flow 36, indicative of an amount of the tracer gas purged from the outlet zone 26, as also further explained below. Finally, the leak testing system 20 includes a processing device 42 in communication with the monitoring device 38 to receive a spectroscopic emission signal 40 representative of the monitored spectroscopic emission. The processing device 42 is configured to allow a determination of a presence of a gas leak between the inlet zone 24 and outlet zone 26 of the gas flow component 22 such as described below. It will however be understood that other system configurations may be used without departing from the scope of the present invention.

Referring to both FIGS. 1 and 2, the method first includes continuously circulating 102 the carrier gas through the outlet zone 26 of the gas flow component 22 to purge the tracer gas from the outlet zone 26.

The method also includes a step of continuously monitoring 104, downstream of the outlet zone 26 of the gas flow component 22, a spectroscopic emission from the carrier gas indicative of the amount of the tracer gas purged from the outlet zone 26.

One skilled in the art will readily understand that at the onset of the testing method described herein, the outlet zone 26 may contain a residual amount of tracer gas. Reference to a residual amount of tracer gas implies that the tracer gas is indeed present in the outlet zone 26, but in a small amount. In some implementations, the method may include pre-purging the outlet zone 26 from atmospheric air before monitoring 104, by circulating the carrier gas through the outlet zone 26. The pre-purging step may be indicated when a high amount of tracer gas is initially present in the outlet zone 26, for example in cases where the tracer gas is of same nature as gases included in atmospheric air, and monitoring of the spectroscopic emission indicative of this high amount is not desired. One skilled in the art will also readily understand that circulation of the carrier gas in the outlet zone results in a gradual purge of the tracer gas initially present in a residual amount or concentration in the outlet zone 26, as the tracer gas in the outlet zone is not replenished.

In some embodiments, the monitoring 104 of the spectroscopic emission is carried out by creating a luminous discharge from the carrier gas. In some implementations, the monitoring device includes a Plasma Emission Detector (PED). By way of further example, the detector may be one of the variants described in U.S. provisional application No. 62/129,231 by GAMACHE, entitled MULTI-MODE PLASMA-BASED GAS DETECTOR USING OPTICAL SPECTROSCOPY, the entire contents of which is incorporated herein by reference. In devices of this type, the gas to be analysed is fed into a plasma chamber, where it undergoes a transformation under an applied excitation field. Chemical compounds are ionised and decomposed by collisions with energetic electrons and molecules and atomic components are excited to higher energy levels, emitting radiation in the de-excitation process characteristic of the spectral properties of the species present in the gas. Processing this radiation can therefore provide information related to the nature and relative concentration of the species in the gas to be analysed.

By tuning the monitoring device to a wavelength known to characterize the tracer gas, the monitored spectroscopic emission can be representative of the presence of the tracer gas only, and contain no or minimal contributions from the carrier gas or/or impurities. Detection of the light from the monitored spectroscopic emission provides the spectroscopic emission signal 40 which can be continuous monitored over time, therefore allows following the variation of the concentration of tracer gas in the carrier gas as the tracer gas is being gradually purged from the outlet zone of the gas flow component. Consequently, the monitored intensity of the spectroscopic emission signal is originally proportional to the residual amount of the tracer gas in the outlet zone. As the purging process continues, the monitored intensity of the spectroscopic emission signal decreases as there is less and less tracer gas carried away from the outlet zone by the carrier gas.

The monitoring device further preferably includes a light detector such as a photodiode or the like, transforming the light emitted by the plasma into a proportional analog or digital signal embodying the spectroscopic emission signal. In one variant, the light detector may be mounted at one or more windows of the plasma chamber so as receive the light from the plasma directly. In another variant, the light from the plasma may be collected into an optical fiber guiding this light for detection away from the plasma chamber.

Detection of the light from the plasma is preferably wavelength-specific, so that the spectroscopic emission signal monitored through the present method includes only the light at the wavelength of wavelengths representative of the tracer gas. Wavelength specificity may be achieved in a variety of manners. In one example, a filter or filters may be provided in a path of the light from the plasma such that only light having the desired spectral contents reaches the photodiode. In other variants different configurations could be used to extract the spectral information from the detected signals, such as for example using a spectrometer or other spectrally resolved detector to convert the optical energy into analog or digital information.

Figure 3A:
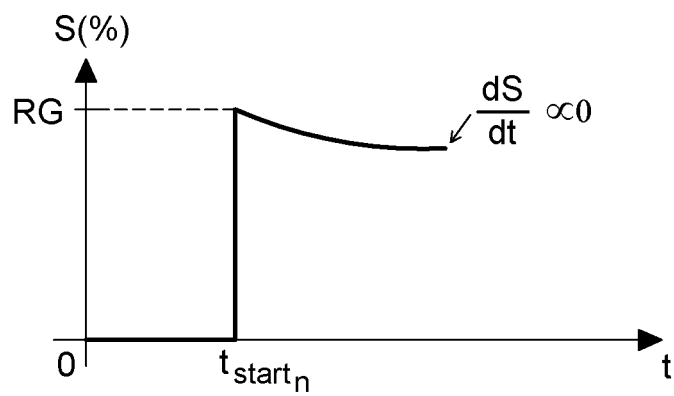
FIGS. 3A to 3C are graphical representations of the evolution of the monitored spectroscopic emission signal during the initial purge of a residual amount of tracer gas (FIG. 3A), after a rescaling step (FIG. 3B), and upon detection of an intensity variation step (FIG. 3C).

Referring to FIG. 3A, the variation of the spectroscopic emission signal over time during the purging stage is graphically illustrated. The monitoring of the spectroscopic emission from the carrier gas is shown as starting at time $t_{STARTn}$ which can for example take place right after the pre-purging step (monitoring cycle n=0). The intensity of the monitored spectroscopic emission signal (S in % of the range of the currently observed scale) at the beginning of the monitoring cycle ($t_{STARTn}$) is indicative of the residual amount of tracer gas resulting from the pre-purging. The residual amount of tracer gas is referred to as residual gas (RG). From the beginning of the monitoring, the intensity of the monitored spectroscopic emission signal keeps decreasing at a slowing rate (dS/dt) until converging towards an asymptote, which corresponds to about dS/dt=0. This decreasing spectroscopic emission from the carrier gas reflects the gradual purge of the residual amount of tracer gas from the outlet zone.

Figure 3B:
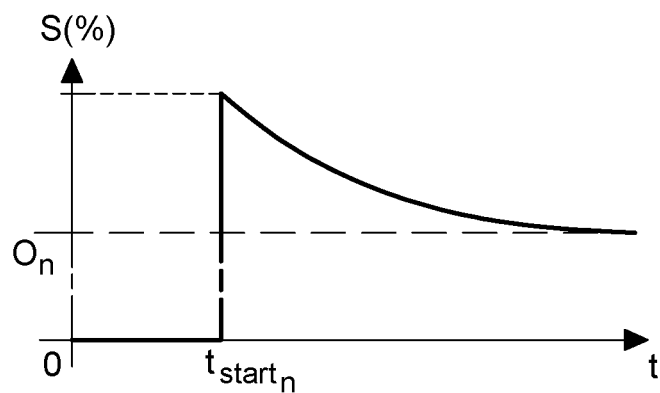

In some implementations, the testing method 100 may include an optional step of re-scaling 106 the spectroscopic emission signal upon the monitoring 104 indicating that a residual amount of said tracer gas has been purged from the outlet zone. FIG. 3B shows the resulting change in the graphical display of the spectroscopic emission signal. In principle, the intensity of the spectroscopic emission signal may be seen as an allocatable variable. When the decreasing rate of the spectroscopic emission tends to be null, the intensity of the spectroscopic emission signal can be allocated with a zero value, serving as a baseline for the subsequent steps of the testing method. According to the graphical display of the spectroscopic emission versus time, the baseline $0_n$ is therefore adjusted in a tare or scaling step 106. The scaling of the graphical display of the monitoring can be repeated several times.

It should be understood that the re-scaling of the spectroscopic emission signal refers to any operation enabling to properly display the intensity variation pattern of the spectroscopic emission. By taring or scaling the spectroscopic emission signal, the display can be tailored so as to distinguish differences related to the intensity variation pattern in the spectroscopic emission signal.

Upon the monitoring indicating that the residual amount of tracer gas has been purged from the outlet zone, the method 100 next includes a step of introducing 107 a test flow 29 of the tracer gas in the inlet zone 24 of the gas flow component 22. As mentioned above, this may for example be accomplished through activating the pressurizing unit 28. In some variants, the tracer gas may be provided from the tracer gas source 27. In other variants, for example when using nitrogen as the tracer gas, the pressurizing unit may simply introduce ambient air into the inlet zone 26 at a controlled pressure.

Figure 3C:
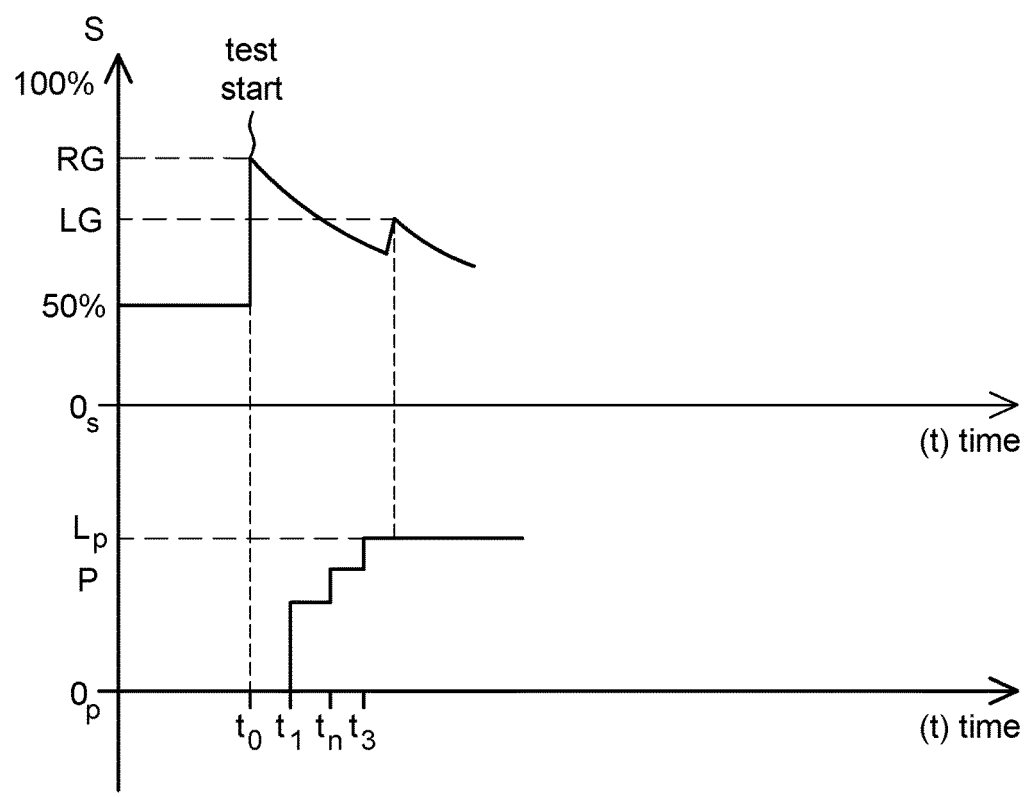

The method 100 next includes increasing 108 the inlet pressure of the gas flow component for successive pressure increments, each pressure increment starting a monitoring cycle. As illustrated in FIG. 3C, the introduction of the test flow of tracer gas into the inlet zone at an incremental increase of inlet pressure can be viewed as setting the beginning of a new monitoring cycle (n=n+1) at a time $t_{START\ n+1}$.

The monitoring of the spectroscopic emission may be seen as a succession of monitoring cycles n, the beginning of a monitoring cycle being set by an incremental increase in the inlet pressure of the tracer gas. Therefore, after each inlet pressure increment, a new residual amount of the tracer gas is determined based on the spectroscopic emission monitored at the beginning of the monitoring cycle.

Each monitoring cycle may have a fixed of variable duration. In one example, each pressure increment is performed after a pre-set operating time.

Alternatively, each pressure increment may be performed after the intensity variation in the spectroscopic emission becomes asymptotic, or after it becomes null.

The method 100 also includes a step of determining 110 a presence of the gas leak between the inlet zone and outlet zone of the gas flow component upon detecting a step variation in the monitored spectroscopic emission following one of the pressure increments in the inlet pressure.

In presence of a leak between the inlet zone 24 and the outlet zone 26 of the gas flow component 22, a step variation in the spectroscopic emission from the carrier gas can be observed. In other words, the behavior of the spectroscopic emission signal will be impacted by the influx of an additional amount of tracer gas in the outlet zone of the gas flow component. When the inlet pressure imposed in the inlet zone 24 is sufficient to let the tracer gas flow from the inlet zone to the outlet zone (through an orifice channel, capillary channel or permeation channel), the amount of tracer gas present in the outlet zone 26 and carried away by the circulating carrier gas suddenly increases. In some circumstances, a sudden increase in the spectroscopic emission signal 40 can also be observed, indicative of the increased residual amount of tracer gas in the output carrier gas flow 36.

As will be readily understood by one skilled in the art, the nature of the behavior change that can be observed in the spectroscopic emission signal will depend on the type of leak present, the type of gas flow component being tested, the operating conditions of the testing system, etc.

High value leaks may be particularly susceptible of detection by observing a sudden increase in the intensity of the spectroscopic emission signal, defining the intensity variation step. This behavior may for example be observed in the presence of an orifice-type leak in through the gas flow component. As mentioned above, an orifice-type leak corresponds to a leak wherein the length of the flow channel is at most identical to its average diameter. Typically, upon a sufficient pressure differential applied between the inlet and the outlet zone of the gas flow component have such an orifice type leak, the tracer gas molecules in the inlet zone will burst through the orifice and flood the outlet zone.

The monitoring of the spectroscopic emission may include displaying, as a function of time, an intensity of a spectroscopic emission signal representative of the monitored spectroscopic emission on a normalized intensity scale. By way of example, referring to FIG. 3C, an example of an intensity step variation in the spectroscopic emission signal following a pressure increment in the inlet pressure is graphically illustrated. It can be seen in the shape of the spectroscopic emission signal S that at time $t_3$, that is, after the third pressure increment, a significant increase in the intensity of the spectroscopic emission signal, defining a variation step, can be observed, and is indicative of the presence of a gas leak from the inlet zone to the outlet zone of the gas flow component. As the only change in the purging conditions between cycle n=2 and n=3 is the influx of tracer gas through the leak, the variation step is only indicative of the leaked amount of tracer gas in the outlet zone. One skilled in the art would readily understand that a variation step in the intensity of the monitored spectroscopic emission signal may be observed in presence of other types of value leaks, causing the amount of tracer gas present in the outlet zone to sufficiently increase to see a variation step in the graphical display.

It should be also understood that the tare is optional and the detection method would still be operable without tare. Without tare, the variation step in the spectroscopic emission would be indicative of the leaked amount of tracer gas in addition to the residual amount of tracer gas in the outlet zone.

In some implementations, each incremental increase in the inlet pressure may be performed after a pre-set operating time during the introduction of the test flow of the tracer gas. Further optionally, the pre-set operating time may be chosen to monitor an asymptotic intensity variation in the spectroscopic emission by the end of said pre-set operating time. The pre-set operating time may be further chosen so that the intensity variation tends to be null by the end of said pre-set operating time (referred to as dS/dt=0 in FIG. 3A).

Leak Testing System

Referring to FIG. 2, there is shown a schematic diagram of a leak testing system 20 for testing for a gas leak between an inlet zone 24 and an outlet zone 26 of a gas flow component 22 in a shut state according to some implementations. As mentioned above, the gas flow component 22 may for example be a valve, such as a diaphragm valve, rotary valve, needle valve, ball valve, etc. The gas flow component may also be embodied by a fitting, a vessel or the like.

Generally speaking, the leak testing system 20 may include a number of interrelated devices and units which are operatively connectable to the gas flow component 22 under test so as to detect a gas leak therethrough. Embodiments of the system can be tailored to detect gas leaks from low value to high value as defined above.

The leak testing system 20 generally includes a pressurizing unit 28 connectable to the gas flow component so as to be in fluid communication with the inlet zone 24. The pressurizing unit 28 is configured to be fed with the tracer gas at atmospheric pressure, optionally from a tracer gas source 27, and to deliver a tracer gas test flow 29 into the inlet zone 24 of the gas flow component 22. The pressurizing unit 28 is operable to increase the inlet pressure of the gas flow component for successive pressure increments.

It should be understood that the pressurizing unit 28 may be embodied by to any device or device assembly enabling to vary the pressure of a fluid flow. Referring by way example to the configuration shown in FIG. 4, in some implementations, the pressurizing 28 unit may include a high pressure electronic pressure controller PC1 for varying the inlet pressure in combination with an absolute pressure transducer PT1 for measuring the inlet pressure. Other variants can of course be considered within the scope of the invention. It should also be understood that the leak testing system 20 may include other pressure-related devices downstream the pressurizing unit, to control or vary the pressure of the carrier gas, tracer gas or combination thereof throughout the system.

The leak testing system 20 further includes a carrier gas flow control assembly 30 in bidirectional fluid communication with the outlet zone 26. The carrier gas flow control assembly 30 is configured to receive an input carrier gas flow 32 from a carrier gas source 34. The input carrier gas flow 32 circulates through the outlet zone 26 of the gas flow component 22, purging tracer gas therefrom, as explained in more detailed below, resulting in an output carrier gas flow 36.

As can be readily understood by one skilled in the art, the pressurizing unit 28 and the carrier gas flow control assembly 30 may include a plurality of valves, for guidance and/or venting purposes in relation to circulation of the tracer gas and of the input and output carrier gas flows 32, 36. In some implementations, the valves may be arranged in series or in parallel and may be switchable between an open position and a closed position to guide or vent the carrier gas, the tracer gas or a combination thereof.

Figure 4:
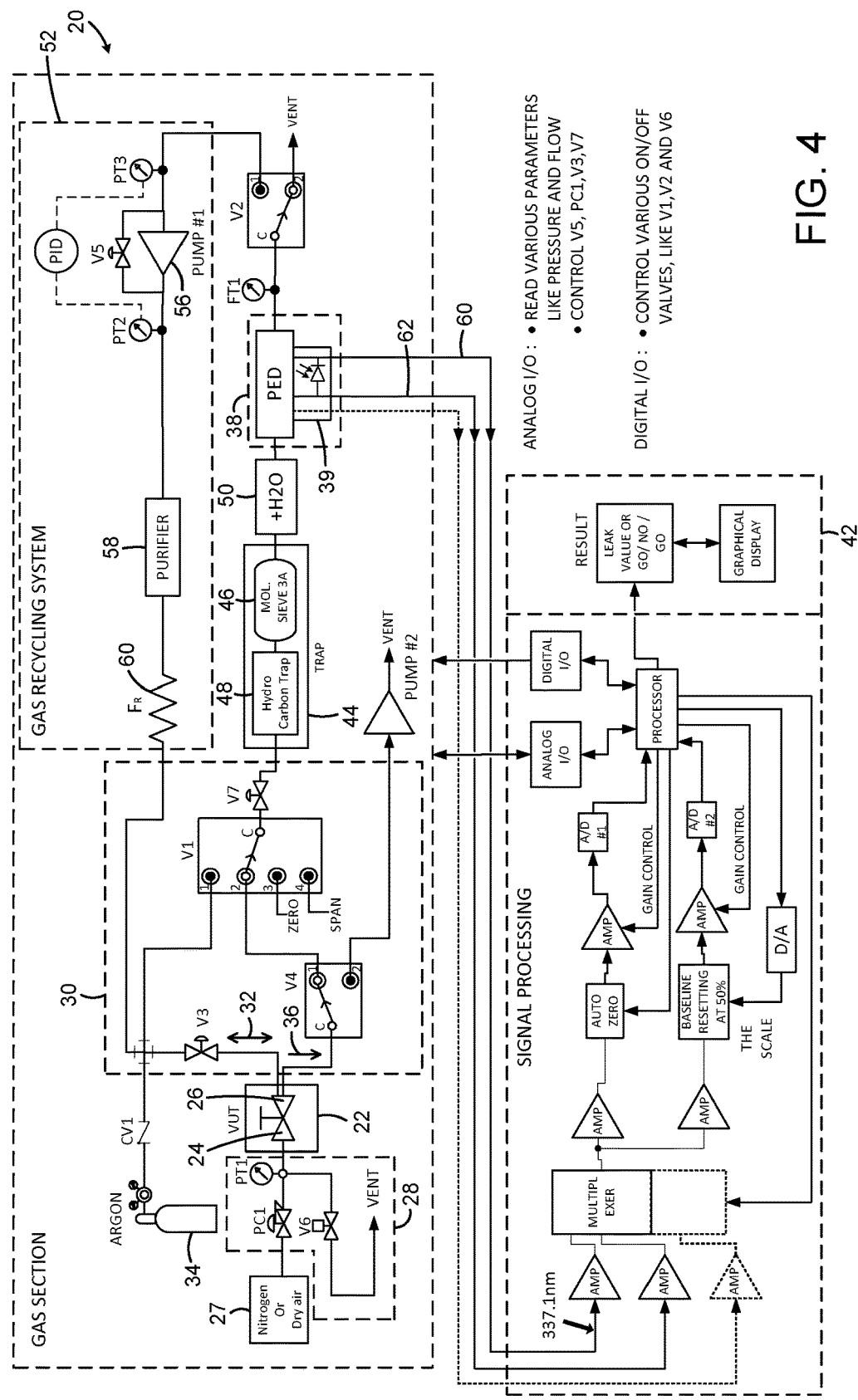
FIG. 4 is a schematic diagram of a gas leak testing system according to one example of implementation.

An exemplary embodiment of the carrier gas flow control assembly 30 is shown in FIG. 4, and includes valves V1, V3 and V4 as well as pressure transducers PT2 and PT3. A more detailed description of the operation of the leak testing system 20 of FIG. 4 is given further below.

The leak testing system 20 further includes a monitoring device 38 connectable to the carrier gas flow control assembly 30 so as to receive the output carrier gas flow 36. The monitoring device 38 is configured to continuously monitor a spectroscopic emission from the output carrier gas flow 36, indicative of an amount of the tracer gas purged from the outlet zone 26. As mentioned above the monitoring device 38 may include a Plasma Emission Detector (PED) in which the spectroscopic emission created through the generation of a luminous plasma discharge from the output carrier gas flow. The monitoring device 38 may further include a light detector such as a photodiode 39 or the like, transforming the light emitted by the plasma into a proportional analog or digital signal embodying the spectroscopic emission signal.

As explained above, the monitoring device 38 is preferably wavelength-specific, and is tuned to a wavelength at which the monitored spectroscopic emission signal 40 is representative of an emission specific to the tracer gas. In some implementations, the monitoring device 38 may be configured to perform multiple-wavelength monitoring. The multiple-wavelength monitoring can provide improved sensibility to various values of gas leak, from low value leaks to high value leaks.

Advantageously, use of a PED enables the monitoring of spectroscopic emission at different wavelengths which are sensitive to different types of gas (like Ar, $N_2$ and $O_2$) or sensitive to different concentrations (or amounts) of a same gas. It should however be understood that the monitoring device is not limited to a PED, and alternatively, a Thermal Conductivity Detector (TCD) or a mass spectrometer can be used without departing from the scope of the present invention. Optionally, the monitoring device 38 may be selected according to the nature of the tracer gas. A PED may be suited to monitor spectroscopic emission from nitrogen and a mass spectrometer may be suited for example to monitor mass-to-charge ratio of ionized helium.

The leak testing system 20 further includes a processing device 42 in communication with the monitoring device 38 to receive the spectroscopic emission signal 40 representative of the monitored spectroscopic emission. The processing device 42 is configured to allow a determination of a presence of a gas leak between the inlet zone 24 and outlet zone 26 of the gas flow component 22 such as described below. An example of a processing device according to one implementation is shown in FIG. 4 and explained further below. It will however be understood that other configurations may be used without departing from the scope of the present invention.

In some implementations, the processing device 38 can include a first signal processing channel 60 and a second signal processing channel 62. Different signal processing channels may be used to process and display the monitored spectroscopic emission signal under different conditions.

In the illustrated implementation of FIG. 4, the first signal processing channel 60 is for example used to display the absolute concentration value of tracer gas in the output carrier gas flow, whereas the second signal processing channel 62 can be used to display a differential value, illustrating the intensity pattern variation in the monitored spectroscopic emission.

For example, the first signal processing channel 60 can be used to display the amount of nitrogen in the carrier gas, therefore providing a direct reading of the level of leak through the gas flow component in ppm of nitrogen. One skilled in the art would readily understand that other engineering units in relation to quantifying the gas leak can be generated through conversion by a microcontroller for example. The second signal processing channel 62 may allow setting the baseline of the displayed spectroscopic emission at 50% of the scale. This rescaling can advantageously enable to accelerate testing operating as a user does not need to wait for a complete evacuation of nitrogen from the outlet zone of the gas flow component to monitor spectroscopic emission at a higher inlet pressure. The processing device 42 reads the actual value of the monitored spectroscopic emission indicative of this residual amount at the beginning of a monitoring cycle, records it and subtracts it from the reading of the subsequent monitoring cycle. Alternatively, in another example of implementation up to 10% of the residual nitrogen amount can be subsequently offset by a 50% downscaling. The operation of the processing device 42 in a differential mode according to two signal processing channels 60 and 62 provides better gas leak detection sensitivity, even if there is a high level of nitrogen already present in the outlet zone 26 of the gas flow component 22.

In some implementations, the processing device 42 can graphically display an indication of the intensity of the spectroscopic emission as seen in the graphs of FIGS. 3A to 3C. The presence of the leak of tracer gas through the gas flow component is detected when the signal displayed by the processing device 42 shows an intensity variation pattern as above defined in the monitored spectroscopic emission signal 40, following a pressure increment in the inlet pressure.

For example, as seen in the graph similar to the one shown in FIG. 3C may be displayed, illustrating a case where a variation step is observed in the monitored spectroscopic emission signal following a given pressure increment. The inlet pressure of the tracer gas at which a leak is detected may be referred to as the leak pressure (LP). At the leak pressure, additional tracer gas enters the outlet zone and this additional amount is gradually carried away from the outlet zone by the carrier gas, such that the step in the monitored spectroscopic emission is indicative of the additional amount of leaked tracer gas.

In some implementation, the output of the testing method may be provided as textual information to the user, providing an indication of the presence or absence of a leak and optionally additional data such as the type of leak detected, the leak pressure, the concentration of tracer gas in the output carrier gas flow, etc. Other visual or auditory outputs may also be considered.

The processing device 42 may include any circuit, chip, processor, or other component that may be used to process the monitored spectroscopic emission signal and determine the presence of a leak. In some implementations, the processing device 42 may be configured to feed the monitored spectroscopic emission 40 to a plurality of amplification stages, tare sections (or offset shifting), range amplifiers, ND converters in combination to a multiplexer and a microcontroller. FIG. 4 illustrates one possible configuration for the processing device, although it will be readily understood that a multitude of other configurations could be envisioned by one skilled in the art.

In some implementations, the monitoring device 38 and the processing device 42 may be configured to support a multi-wavelength scheme such as described above. In one example, in order to achieve multiple-wavelength monitoring different interference band pass optical filters can be used in the path of the optical emission from the plasma chamber to filter out the required wavelengths prior to detection of the signal by a photodiode. On the other side of each interference filter, the photodiode can be connected to an operational amplifier to constitute one monitoring channel. For example, three monitoring channels could be differently configured. Each one of the monitoring channels of the monitoring device 38 can be connected to an analog multiplexer of the processing device 42 to allow individual channel selection as needed. The analog multiplexer can be controlled by a microcontroller, as seen on FIG. 4.

It will be readily understood that the leak testing system may include other components, devices assemblies or the like performing additional and/complementary functions to those described above without departing from the scope of the invention.

With particular reference to FIG. 4, the leak testing system 20 according to the illustrated embodiment for example includes a sieving assembly 44 operatively connected to the outlet zone 26 of the gas flow component through the carrier gas flow control assembly 30 to sieve the output carrier gas flow 36 upstream of the monitoring device 38. The sieving assembly 44 may include any device or device assembly configured to eliminate contaminants from the output carrier gas flow 36 that may affect the spectroscopic emission signal 40. For example, the monitoring of the spectroscopic emission may be affected by excessive moisture or hydrocarbon content of the carrier gas. Moisture pollution does not necessarily damage the monitoring device 38, but may slow down the response time of the monitoring device 38 and increases noise and reduce sensitivity of the monitored spectroscopic emission signal 40.

In some implementations, the sieving assembly 44 may include a moisture trap 46, a hydrocarbon trap 48 or a combination thereof. The moisture trap 46 can for example be useful upstream of a PED since the luminous discharge generated by the plasma may be affected by moisture. In one implementation, when the tracer gas is nitrogen for example, the moisture trap may be embodied molecular sieve having 3 Å of diameter to avoid trapping nitrogen that has a molecular size of about 4 Å. The hydrocarbon trap 46 can include an activated charcoal, a nickel-based catalyst or any other hydrocarbon active gettering material.

In some implementations, the system 20 may also include a moisture doping device 50 operatively connectable to the outlet zone of the gas flow component to provide a doping amount of water to the output carrier gas flow 36 upstream of the monitoring device 38. In combination with the moisture trap 46 from the sieving assembly 44, an addition of few ppm of water can be sufficient to dope moisture of the carrier gas and render the monitoring device, such as a PED, insensitive to moisture pollution. For example, 3 to 8 ppm of water may be added to the output carrier gas flow. Alternatively, moisture can be added through a permeation tube, or directly through the PED having at least one wall permeable to water, thereby releasing moisture directly in the plasma chamber.

In some implementations, the leak testing system may include any device or device assembly to recover the carrier gas exiting the monitoring device. In some instances, it may for example be economical or desired to recycle the remaining carrier gas after it has been used to carry the tracer gas through the monitoring device, so as to reuse the same carrier gas as a carrier gas source for the leak testing system. In the illustrated embodiment of FIG. 4, the leak testing system 20 therefore include a gas recycling assembly 52 located downstream of the monitoring device 38 for receiving a remaining carrier gas flow 54 exiting the monitoring device 38.

The remaining carrier gas flow 54, which may still include some traces of the tracer gas, can for example be made usable again by mixing with clean carrier gas from the input carrier gas flow 32, diluting the proportion of tracer gas in the remaining carrier gas flow down to a negligible and/or acceptable amount.

Optionally, the gas recycling assembly 52 can include a pump 56, a gas purifier 58, a flow restrictor 60 or a combination thereof. The pump 56 preferably drives the remaining carrier gas flow to be reinserted into the outlet zone 26 of the gas flow component 26 through the carrier gas flow control assembly 30. The gas purifier 58 is for removing at least a part of the residual amount of tracer gas from the carrier gas by molecular sieving. The flow restrictor 60 is provided downstream of the pump 56 and purifier 58, to provide an adequate flow rate of carrier gas out of the gas recycling assembly 52. Further optionally, the flow restrictor may be a capillary flow orifice or a disc-type flow orifice.

In some implementations, the leak testing system 20 may be configured to be portable such that it facilitates transport and connectivity to the gas flow component under test. It should be understood that portable refers to the capacity of being transported unto any location where a gas leak is suspected by minimizing the number and size of equipment included in the system.

It is worth mentioning that throughout the following description when the article "a" is used to introduce an element it does not have the meaning of "only one" it rather means of "one or more". For instance, the system according to the invention may include one or more gas flow components under test in connection to respective one or more monitoring devices without departing from the scope of the present invention.

It should be understood that any one of the above mentioned optional aspects of each system and method may be combined with any other of the aspects thereof, unless two aspects clearly cannot be combined due to their mutually exclusivity. For example, the various operational steps of the method and/or structural elements of the system as described herein-above, herein-below and/or in the appended Figures, may be combined with any of the general method and system descriptions in accordance with the appended claims.

Testing Method Using Volume Flow Rate Control

In accordance with another aspect, there is provided a method of testing for a gas leak between an inlet zone and an outlet zone of a gas flow component in a shut state, which uses decrements in the volume flow rate of carrier gas as opposed to increment in the inlet pressure. The volume flow rate can be defined as the volume of fluid passing through per unit of time.

As will be readily understood in the art, the intensity of a spectroscopic emission representative of the tracer gas being purged from the outlet zone is directly related to the amount of tracer gas molecules of the tracer species per unit volume in the plasma chamber of the plasma emission detector. In the previously described implementation, changing the inlet pressure results in an influx of additional molecules of tracer gas in the outlet zone in the presence of a leak, resulting of a greater proportion of molecules of tracer gas in the plasma chamber for a same volume, hence increasing the intensity of the spectroscopic emission as explained above. A similar effect can also be obtained by decreasing the total volume of gas in the plasma chamber, while keeping the amount of tracer gas molecules constant.

Figure 5:
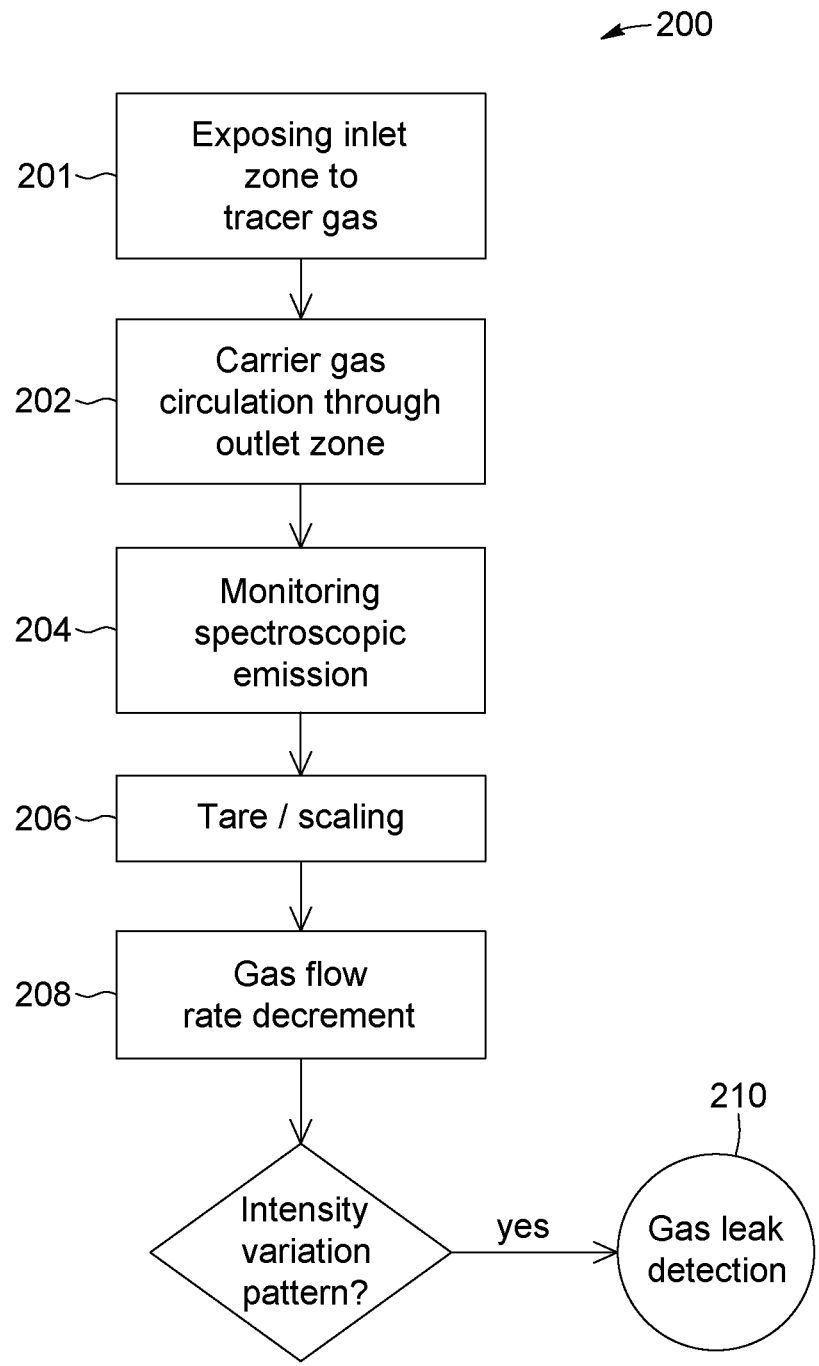
FIG. 5 is a schematic diagram of the gas leak testing method steps according to another embodiment of the present invention.

Referring to FIG. 5, a flow chart illustrating the steps of a method 200 according to this implementation is shown. The method according to this implementation first includes exposing 201 the inlet zone of the gas flow component to the tracer gas. This may be carried out by introducing a test flow of tracer gas in the inlet zone at a constant pressure. In other variants, for example using nitrogen as the tracer gas, this step may simply be achieved by exposing the inlet zone to ambient air. It will be readily understood that this variant may be of particular interest in the absence of means to control the inlet pressure or when such a control is undesired or unavailable.

The method 200 next includes circulating 202 the carrier gas through the outlet zone of the gas flow component to purge the tracer gas from the outlet zone according to a constant volume flow rate. As explained above, this may be performed by providing a carrier gas source in fluid communication with the outlet zone of the gas component. The carrier gas may be argon, helium or other suitable gas species.

The method 200 next includes monitoring 204, using a plasma emission detector downstream of the outlet zone, a spectroscopic emission from the carrier gas indicative of an amount of the tracer gas purged from the outlet zone.

One skilled in the art will readily understand that at the onset of the present testing method, the outlet zone may contain a residual amount of tracer gas. Reference to a residual amount of tracer gas implies that the tracer gas is indeed present in the outlet zone, but in a small amount. In some implementations, the method may include pre-purging the outlet zone from atmospheric air, by circulating the carrier gas through the outlet zone. The pre-purging step may be indicated when a high amount of tracer gas is initially present in the outlet zone, for example in cases where the tracer gas is of same nature as gases included in atmospheric air, and monitoring of the spectroscopic emission indicative of this high amount is not desired. One skilled in the art will also readily understand that circulation of the carrier gas in the outlet zone results in a gradual purge of the tracer gas initially present in a residual amount or concentration in the outlet zone, but that there may remain a small amount of tracer gas in the carrier gas flow in case of a leak, as tracer gas may enter the outlet zone of the gas flow component through the leak. Preferably, the purging of the outlet zone is performed until the slope of the variation in intensity of the monitored spectroscopic emission is constant, and preferably null or close to null. One or more optional tare/scaling steps may be performed in order to re-adjust the baseline of the graphical display of the monitored spectroscopic emission signal.

Upon the monitoring indicating that a residual amount of said tracer gas has been purged from the outlet zone, the method next includes decreasing 208 the volume flow rate of the carrier gas for at least one flow rate decrement. In the absence of a leak, this step does not have any impact on the intensity of the monitored spectroscopic emission. However, as explained above, if a flow of tracer gas leaks through the gas flow component into the outlet zone then this step will increase the relative proportion of tracer gas in the gas volume in the plasma chamber, and increase the intensity of the monitored spectroscopic emission, creating a step variation. The presence of a gas leak between the inlet zone and outlet zone of the gas flow component is determined 210 upon detecting a step in the monitored spectroscopic emission following the flow rate decrement.

Multi-wavelength Implementations

Optionally, the leak testing method may involve monitoring the spectroscopic emission from the output carrier gas flow at multiple wavelengths.

In according with such a variant, there is provided a method of testing for a gas leak between an inlet zone and an outlet zone of a gas flow component in a shut state, the method using a tracer gas and a carrier gas different from the tracer gas. The method first includes circulating the carrier gas through the outlet zone of the gas flow component to purge the tracer gas from the outlet zone. Then the method includes exposing the inlet zone of the gas flow component to the tracer gas. The method also includes parallelly monitoring, using a plasma emission detector downstream of the outlet zone, a spectroscopic emission from the carrier gas indicative of an amount of the tracer gas purged from the outlet zone at a first wavelength and at a second wavelength respectively sensitive to a first range and a second range of the tracer gas concentration in the outlet zone of the component.

In one implementation, the monitoring device and processing device may be configured to monitor a first and a second wavelength, respectively sensitive to a first range and a second range of the tracer gas concentration in the outlet zone of the gas flow component. As is known in the art, different spectroscopic lines in the characteristic spectrum of a given species have different strengths. Different spectroscopic lines can therefore be used to monitor the presence of the tracer gas in different concentration ranges. For example, when the tracer gas is nitrogen, a spectroscopic emission from the carrier gas at the first wavelength of 337.1 nm can be indicative of a nitrogen concentration of 0 ppm to 1000 ppm, whereas a spectroscopic emission at a second wavelength of 391 nm is indicative of a nitrogen concentration between 1000 ppm to 10,000 ppm. It should be noted that the 357.69 nm wavelength can be also selected to monitor nitrogen, as this wavelength is much less subject to interference with hydrocarbons that may be included in the carrier gas. For example, presence of hydrocarbons may be an issue when testing gas flow components having grease or oil trace.

Additional wavelengths may be monitored to provide sensitivity in additional concentration ranges. Still using the example of nitrogen as the tracer gas, a third wavelength of 406 nm can get improved results and a more linear response for high concentrations of nitrogen up to 10,000 ppm.

Additional Variant

In some implementations, the method can include introducing a test flow of at least two tracer gases during monitoring of the spectroscopic emission from the carrier gas, so as to vary detection sensibility and therefore provide suitable detection of gas leaks of various magnitudes.

Exemplary Implementations

Exemplary implementations of the system described above, connected to a valve, are schematically illustrated in FIG. 4. An exemplary implementation of the method, in connection to the exemplary system, is also described below.

In this example, the gas flow component 22 is embodied by a valve. The inlet zone 24 of the valve under test (VUT) is connected to a source of nitrogen $N_2$ or air as the tracer gas source 27. Once the system is secured to the valve under test (VUT), operation starts with the valve under test (VUT) being in a closed or shut position such that the inlet zone 24 may not be in fluid communication with the outlet zone 26 (without the presence of a gas leak in the valve under test (VUT)).

Optionally, the system can include a plurality of valves V1 to V7 to either guide or vent the tracer gas and/or carrier gas. It should be understood that the valve under test (VUT) refers to the gas flow component under test and is not included in the valve assembly. V1, V2 and V4 are at least switchable between an open position for venting the tracer gas or the carrier gas to the atmosphere, and a closed position for guiding the carrier gas and tracer gas to the plasma emission detector (PED) of the monitoring device 38 or the outlet zone 26 of the valve under test (VUT). V3, V5, V6 and V7 guide tracer gas and/or carrier gas to the outlet zone 26 of the valve under test (VUT) or to vent to the atmosphere. Operability of valves Vi to V6 will be further described below.

Pre-purging

When the valve V3 is in open position, the outlet zone 26 of the valve under test (VUT) is in fluid communication with argon, as carrier gas, so as to purge residual nitrogen or air from the outlet zone 26. The valve V4 is in position 2 (open position) and PUMP#2 is activated so as to vent to the atmosphere argon gradually purging residual nitrogen or air. The valve V4 may be operated according to static purging or dilution purging, i.e. the valve V4 is switched alternately between position 1 and position 2, resulting in pressure pulsing and dilution of residual nitrogen or air. After 5 to 10 iterations, for example, the valve V4 may be switched to a closed position (position 1) when reaching an acceptable residual amount of nitrogen or air in the outlet zone 26 of the valve under test (VUT), such that the outlet zone 26 can be in fluid communication with downstream equipment, including the plasma emission detector (PED), according to a series of valves.

Calibration

In some implementations, the plasma emission detector (PED) can be calibrated according to the following procedure. A zero gas and a span gas can be used for calibration. When the valve V1 is in position 3, the zero gas is allowed to flow through the plasma emission detector PED. The zero gas can be of the same nature as the carrier gas, i.e. argon, and includes no or very low pre-determined concentration of tracer gas, i.e. nitrogen. The monitored spectroscopic emission from the zero gas will serve as zero value for the rest of the monitoring until next calibration. The valve V1 is then put in position 4 to allow the span gas to flow through the plasma emission detector PED. The span gas is a gas which includes a known concentration of tracer gas, i.e. nitrogen, which is substantially higher than the concentration in the zero gas. The monitored spectroscopic emission from the span gas is recorded as a span value, which is representative of a known and calibrated concentration of nitrogen. These zero and span values of the spectroscopic emission intensity are then used to establish a calibration curve. The signal processing unit of the system, located downstream the plasma emission detector (PED), can include an analog to digital converter count so as to convert counts to ppm value of tracer gas.

In some implementations, the plasma emission detector (PED) can be recalibrated periodically to ensure accuracy of the tracer gas concentration based on the monitored spectroscopic emission.

Spectroscopic Emission Monitoring

The valve V1 is switched on position 2, such that the argon coming through V3 and from the outlet zone 26 of the valve under test (VUT) can undergo moisture and hydrocarbon sieving in the sieving assembly 44, moisture doping in the moisture doping device 50, before reaching the plasma emission detector PED. A carrier gas flow measuring device FT1 may be operatively connected to an outlet of the plasma emission detector (PED). Argon gradually purges the outlet zone 26 of the valve under test (VUT) from a residual amount of nitrogen, as tracer gas. The plasma emission detector is therefore tuned to monitor spectroscopic emission of nitrogen from argon.

The monitored value of the spectroscopic emission is sent to the processing device 42 of the system, located downstream the plasma emission detector (PED). The processing device 42 graphically displays the monitored spectroscopic emission according to operation time. As spectroscopic emission of residual nitrogen from argon comes from the gradual purge of the outlet zone 26 of the valve under test (VUT), monitored spectroscopic emission of residual nitrogen gradually decreases as seen on FIG. 3A. During this operation phase, the inlet zone 24 of the valve under test (VUT) is at atmospheric pressure and the gas leak rate is supposed to be null or extremely low. Therefore, the monitored spectroscopic emission is only indicative of the residual nitrogen from the outlet zone 26.

Tare/Scaling

The spectroscopic emission baseline is re-zeroed (tare) or off-set (scaling) according to the monitored spectroscopic emission indicative of the residual amount of nitrogen in the outlet zone 26 of the valve under test (VUT). Therefore, subsequent variation in the reading of the monitored spectroscopic emission will be indicative of the presence of an additional source of nitrogen. Furthermore, the graphical display can be tailored through this process to a scale appropriate to distinguish differences in the intensity variation pattern in the signal, as seen in FIG. 3B.

Incremental Pressurization

Additional nitrogen can flow from the inlet zone 24 to the outlet zone 26 of the valve under test (VUT) at higher inlet pressures as will be described further below.

The pressurizing unit 28, including a pressure controller (PC1) and a first pressure transducer (PT1), incrementally increases the inlet pressure in the inlet zone 24 of the valve under test (VUT). The value of the inlet pressure increments may depend on the nature and size of the valve under test (VUT).

For example, assuming that the valve under test (VUT) has a working pressure of 1000 psig, the inlet pressure can be incrementally increased by 100 psi increments. Thus, the pressure controller (PC1) creates a nitrogen flow having an inlet pressure rising from 100 to 1000 psig with 100 psi increments. Optionally, the inlet pressure is incrementally increased after a pre-set operation time between each pressure increment. The pre-set operation time can be chosen according to the type of the valve under test (VUT). Larger valves can have longer pre-set operation time.

Following an incremental increase of the inlet pressure, the plasma emission detector (PED) can monitor a varying spectroscopic emission from the nitrogen carried by the argon. The processing device 42 receives the monitored spectroscopic emission and can detect the presence of a gas leak upon displaying an intensity variation pattern in the monitored spectroscopic emission of nitrogen from the flowing argon.

The processing device 42 can also display a step change in the monitored spectroscopic emission and/or a diminution in the slope value of the decreasing spectroscopic emission as there is additional nitrogen flowing through the leak of the valve under test (VUT).

For example, the difference between the decreasing rate of the monitored spectroscopic emission in a non-leaking state and in the leaking state can be calculated and processed to indicate the leaked amount of nitrogen (in a desired leak rate engineering unit). Additionally, a limit decreasing profile of the spectroscopic emission can be set above the monitored spectroscopic emission to provide an acceptable nitrogen leak rate upper limit.

Before each incremental increase of the inlet pressure, the processing system is configured to rescale or re-zeroed the baseline of the displayed spectroscopic emission, so that subsequent monitoring is performed within a value range indicative of the leaked amount of nitrogen.

For example, the value of the monitored spectroscopic emission indicative of the amount of nitrogen before the incremental increase of the inlet pressure (and after the pre-set operation time) may be subtracted from the value of the monitored spectroscopic emission indicative of the amount of nitrogen after the incremental increase of the inlet pressure.

Further optionally, the value of the monitored spectroscopic emission indicative of the amount of nitrogen before the incremental increase of the inlet pressure could be downsized to a 50% value.

Further optionally, the processing device 42 can be configured to perform an automatic rescaling. For example, when the value of the monitored spectroscopic emission indicative of the amount of nitrogen decreases below a pre-set value, the baseline line can be automatically reset at 50% of the scale, so as to keep the monitored spectroscopic emission on the monitored scale.

Gas Recycling

Still referring to FIG. 4, the gas recycling assembly 52 includes a pump 56 (also identified as PUMP#1), a purifier 58 and a flow restrictor 60. The pump 56 is used to increase the gas pressure, read by a second pressure transducer (PT2), at the value required to maintain the desired gas flow through the flow restrictor 60 which is read by the flow transducer (FT1).

The valve V5 is used to by-pass gas from the pump 56 in order to manage the pump discharge pressure, such that the flow restrictor 60 provides an adequate gas flow based on the pressure read by the second pressure transducer (PT2).

A third pressure transducer (PT3) reads the vent pressure of the plasma emission detector (PED) when using the gas recycling assembly 52. The third pressure transducer (PT3) is an absolute pressure transducer. It should be noted that in this embodiment the operating pressure of the plasma emission detector (PED) is to be maintained at a constant value, since the operating pressure naturally tends to decrease due to pumping action or opening of V5 during gas recirculation. As pressure variation can cause an important baseline shift in the displayed monitored spectroscopic emission, operation of the third pressure transducer (PT3) has priority over operation of the second pressure transducer (PT2).

Optionally, the gas purifier 58 of the gas recycling assembly 52 is configured to trap nitrogen, oxygen, water and hydrocarbons below an acceptable level. The gas purifier 58 can include a first bed of molecular sieve 13× to eliminate H$_2$O, in series with a second bed of nickel or copper catalyst for O$_2$ scavenging, and finally a third bed of zirconium alloy used to eliminate nitrogen.

Final Depressurization

Following the last incremental increase of the inlet pressure, the pressure controller (PC1) is closed and the valve V6 is opened to depressurize the inlet zone 24 of the valve under test (VUT).

Simultaneously, the valve V1 is switched to position 1 to allow pure argon to flow through the plasma emission detector (PED) so as to tare the processing device 42 in order to be prepared for another cycle of test if needed.

Simultaneously, the valve V3 is closed to stop argon from flowing through the outlet zone 26 of the valve under test (VUT).

Finally, valves V1 and V2 can be closed to isolate the plasma emission detector (PED), i.e. to fill the plasma emission detector (PED) with stagnant clean argon.

The detector (PED) can then be shut down until a test is needed for another gas flow component.

Of course, numerous modifications could be made to the embodiments described above without departing from the scope of the invention as defined in the appended claims.

The invention claimed is:

1. A method of testing for a gas leak between an inlet zone and an outlet zone of a gas flow component in a shut state, the method using a tracer gas and a carrier gas different from the tracer gas, the method comprising:
   circulating the carrier gas through the outlet zone of the gas flow component to purge the tracer gas from said outlet zone;
   monitoring, using a plasma emission detector downstream of the outlet zone, a spectroscopic emission from the carrier gas indicative of an amount of the tracer gas purged from the outlet zone;
   upon said monitoring indicating that a residual amount of said tracer gas has been purged from the outlet zone, introducing a test flow of the tracer gas in the inlet zone of the gas flow component;
   increasing an inlet pressure of the gas flow component for at least one pressure increment; and
   determining a presence of a gas leak between the inlet zone and outlet zone of the gas flow component upon detecting a step variation in the monitored spectroscopic emission following one of said pressure increments in the inlet pressure.

2. The method of claim 1, comprising a preliminary step of pre-purging the outlet zone of atmospheric air.

3. The method of claim 1, wherein the carrier gas consist of argon and the tracer gas consist of nitrogen.

4. The method of claim 1, wherein the carrier gas consist of helium and the tracer gas consist of argon.

5. The method of claim 1, wherein the step of monitoring the spectroscopic emission comprises displaying, as a function of time, an intensity of a spectroscopic emission signal representative of said monitored spectroscopic emission on a normalized intensity scale.

6. The method of claim 5, comprising a step of re-scaling the spectroscopic emission signal upon said monitoring indicating that the residual amount of said tracer gas has been purged from the outlet zone.

7. The method of claim 1, wherein the step of monitoring the spectroscopic emission comprises parallelly monitoring the spectroscopic emission at a first wavelength and at a second wavelength respectively sensitive to a first range and a second range of the tracer gas concentration in the outlet zone of the component.

8. The method of claim 1, comprising recycling the carrier gas to the outlet zone after monitoring the spectroscopic emission.

9. A leak testing system for testing for a gas leak between an inlet zone and an outlet zone of a gas flow component in a shut state using a tracer gas and a carrier gas different from the tracer gas, the system comprising:
   a pressurizing unit connectable to the gas flow component so as to be in fluid communication with the inlet zone of the gas flow component, the pressurizing unit being configured to be fed with the tracer gas and to deliver a test flow of said tracer gas into the inlet zone of the gas flow component, the pressurizing unit being operable to increase an inlet pressure of the gas flow component for successive pressure increments;
   a carrier gas flow control assembly connectable to the gas flow component so as to be in bidirectional fluid communication with the outlet zone of the gas flow component, the carrier gas flow control assembly being configured to receive an input carrier gas flow and circulate the same through the outlet zone of the gas flow component to purge the tracer gas from said outlet zone, resulting in an output carrier gas flow;
   a monitoring device connectable to the carrier gas flow control assembly so as to receive the output carrier gas flow, the monitoring device comprising a plasma emission detector and being configured to monitor a spectroscopic emission from the output carrier gas flow indicative of an amount of the tracer gas purged from the outlet zone; and
   a processing device in communication with the monitoring device to receive the monitored spectroscopic emission therefrom, the processing device being configured to allow a determination of a presence of a gas leak between the inlet zone and outlet zone of the gas flow component upon detecting an intensity variation pattern in the monitored spectroscopic emission following one of said pressure increments in the inlet pressure.

10. The system of claim 9, comprising a sieving assembly operable to sieve the output carrier gas flow upstream of the monitoring device, the sieving assembly comprising at least one of a moisture trap and a hydrocarbon trap.

11. The system of claim 9, further comprising a moisture doping device operable to provide a doping amount of water to the output carrier gas flow upstream of the monitoring device.

12. The system of claim 9, wherein the pressurizing unit comprises a pressure transducer for measuring the inlet pressure and a high pressure electronic pressure controller for varying the inlet pressure.

13. The system of claim 9, wherein the carrier gas flow control assembly is switchable between:
   an open position for venting the output carrier gas flow to the atmosphere, and
   a closed position for guiding the output carrier gas flow to the monitoring device.

14. The system of claim 9, wherein the processing device comprises a first signal processing channel and a second signal processing channel, respectively configured to monitor the spectroscopic emission at a first wavelength and at a second wavelength respectively sensitive to a first range and a second range of the tracer gas concentration in the outlet zone of the component.

15. The system of claim 9, further comprising a gas recycling assembly downstream of the monitoring device, to recycle at least a part of the carrier gas from the monitoring device to the outlet zone of the gas flow component.

16. The system of claim 9, wherein the monitoring device further comprises a photodiode transforming light emitted by a plasma within the Plasma Emission Detector into a proportional analog or digital signal.

17. A method of testing for a gas leak between an inlet zone and an outlet zone of a gas flow component in a shut state, the method using a tracer gas and a carrier gas different from the tracer gas, the method comprising:
  exposing the inlet zone of the gas flow component to the tracer gas;
  circulating the carrier gas through the outlet zone of the gas flow component to purge the tracer gas from said outlet zone according to a constant volume flow rate;
  monitoring, using a plasma emission detector downstream of the outlet zone, a spectroscopic emission from the carrier gas indicative of an amount of the tracer gas purged from the outlet zone;
  upon said monitoring indicating that a residual amount of said tracer gas has been purged from the outlet zone, decreasing the volume flow rate of the carrier gas for at least one flow rate decrement; and
  determining a presence of a gas leak between the inlet zone and outlet zone of the gas flow component upon detecting a step in the monitored spectroscopic emission following one of said volume flow rate decrement.

18. The method of claim 17, comprising a preliminary step of pre-purging the outlet zone of atmospheric air.

19. The method of claim 17, wherein the tracer gas consist of nitrogen and the step of exposing the inlet zone of the gas flow component to the tracer gas comprises exposing said inlet zone to ambient air.

20. The method of claim 19, wherein the carrier gas consists of argon.

21. The method of claim 17, wherein the step of monitoring the spectroscopic emission comprises displaying, as a function of time, an intensity of a spectroscopic emission signal representative of said monitored spectroscopic emission on a normalized intensity scale.

22. The method of claim 21, comprising a step of re-scaling the spectroscopic emission signal prior to said at least one flow rate decrement.

23. The method of claim 17, wherein the step of monitoring the spectroscopic emission comprises parallelly monitoring the spectroscopic emission at a first wavelength and at a second wavelength respectively sensitive to a first range and a second range of the tracer gas concentration in the outlet zone of the component.

24. The method of claim 17, comprising recycling the carrier gas to the outlet zone after monitoring the spectroscopic emission.

25. A method of testing for a gas leak between an inlet zone and an outlet zone of a gas flow component in a shut state, the method using a tracer gas and a carrier gas different from the tracer gas, the method comprising:
  circulating the carrier gas through the outlet zone of the gas flow component to purge the tracer gas from said outlet zone;
  exposing the inlet zone of the gas flow component to the tracer gas;
  parallelly monitoring, using a plasma emission detector downstream of the outlet zone, a spectroscopic emission from the carrier gas indicative of an amount of the tracer gas purged from the outlet zone at a first wavelength and at a second wavelength respectively sensitive to a first range and a second range of the tracer gas concentration in the outlet zone of the component.

26. The method of claim 25, wherein the carrier gas consists of argon and the tracer gas consists of nitrogen.

27. The method of claim 25, wherein the tracer gas is nitrogen, and wherein the first and second wavelengths are selected from nitrogen spectroscopic lines at 337.1 nm, 391.0 nm.

28. The method of claim 25, wherein the carrier gas consists of helium and the tracer gas consists of argon.

29. The method of claim 25, wherein the step of monitoring the spectroscopic emission comprises displaying, as a function of time, an intensity of a spectroscopic emission signal representative of said monitored spectroscopic emission at each of the first and second wavelengths on a corresponding normalized intensity scale.

* * * * *